(12) United States Patent
Drabb, Jr.

(10) Patent No.: US 6,180,797 B1
(45) Date of Patent: Jan. 30, 2001

(54) PROCESS FOR THE DEHALOGENATION OF THIOCHROMAN AND DIHYDROBENZOTHIOPHENE DERIVATIVES

(75) Inventor: Thomas Walter Drabb, Jr., Trenton, NJ (US)

(73) Assignee: American Cyanamid Co., Madison, NJ (US)

( * ) Notice: Under 35 U.S.C. 154(b), the term of this patent shall be extended for 0 days.

(21) Appl. No.: 09/542,353

(22) Filed: Apr. 4, 2000

Related U.S. Application Data

(60) Provisional application No. 60/128,009, filed on Apr. 6, 1999.

(51) Int. Cl.⁷ .................. C07D 335/06; C07D 409/02
(52) U.S. Cl. ..................... 548/364.4; 549/23; 549/57
(58) Field of Search ..................... 549/23, 57; 548/364.4

(56) References Cited

U.S. PATENT DOCUMENTS

| | | | |
|---|---|---|---|
| 5,506,194 | 4/1996 | Nasuno et al. | 504/282 |
| 5,607,898 | 3/1997 | Nakumura et al. | 504/282 |

FOREIGN PATENT DOCUMENTS

WO 97/08164    3/1997   (WO) .

OTHER PUBLICATIONS

Anwer, M.K. and Spatola, A.F., Tetrahedron Letters, 26 (11), pp. 1391–1384 (1985).

*Primary Examiner*—Robert W. Ramsuer
(74) *Attorney, Agent, or Firm*—John W. Hogan Jr.; Barbara V. Maurer

(57) ABSTRACT

There is provided a process for the dehalogenation of a compound of formula II via the use of a transition metal catalyst and ammonium formate at atmospheric pressure.

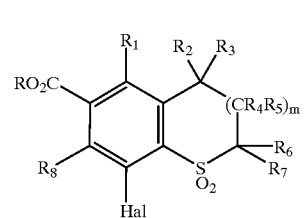

(II)

15 Claims, No Drawings

PROCESS FOR THE DEHALOGENATION OF THIOCHROMAN AND DIHYDROBENZOTHIOPHENE DERIVATIVES

This application claims the benefit of Provisional application 60/128,009 filed Apr. 6, 1999.

BACKGROUND OF THE INVENTION

Thiochroman and dihydrobenzothiophene herbicidal agents and methods of their preparation are described in U.S. Pat. No. 5,506,194, U.S. Pat. No. 5,607,898 and WO 97/08164 among other publications. The 6-(arylcarbonyl) thiochroman and 5-(arylcarbonyl)dihydrobenzothiophene derivatives are effective herbicidal agents at low rates of application and demonstrate selective control of noxious weeds in the presence of important economic crops such as corn and rice.

A common route to prepare these useful herbicidal agents entails the dehalogenation of an 8-halo-6-carbethoxythiochroman or 7-halo-5-carbethoxydihydrobenzothiophene intermediate compound. Heretofore, methods to dehalogenate said intermediate compound required high pressure hydrogenation techniques. Further, product yield and quality may be less than satisfactory. The importance of the dehalogenated 6-carbethoxythiochroman and 5-carbethoxydihydrobenzothiophene intermediates, particularly as key intermediates in the manufacture of herbicidal arylcarbonylthiochroman and arylcarbonyldihydrobenzothiophene agents, creates a significant need in the art for alternative and effective processes for their preparation.

SUMMARY OF THE INVENTION

The present invention provides a safe efficient process for the preparation of a compound of formula I

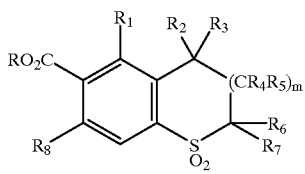

(I)

wherein

R and $R_1$ are each independently H or $C_1$–$C_4$alkyl;

$R_2$ and $R_3$ are each independently H, $C_1$–$C_4$alkyl or $R_2$ and $R_3$ may be taken together with the atom to which they are attached to form a group C=$NOR_9$ or C=O;

$R_4$, $R_5$, $R_6$, $R_7$, $R_8$ and $R_9$ are each independently H or $C_1$–$C_4$alkyl; and m is 0 or 1 which process comprises reacting a compound of formula II

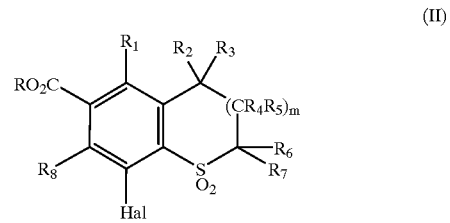

(II)

wherein Hal is Cl, Br or I and R, $R_1$, $R_2$, $R_3$, $R_4$, $R_5$, $R_6$, $R_7$, $R_8$ and m are as described hereinabove with a catalytic amount of Pd/C and at least two molar equivalents of ammonium formate in the presence of a polar solvent optionally at an elevated temperature.

DETAILED DESCRIPTION OF THE INVENTION

Compounds of formula I are important key intermediates in the manufacture of thiochroman and dihydrobenzothiophene herbicidal agents. Methods to prepare the formula I intermediates commonly require high pressure hydrogenation procedures which may give less than satisfactory product yield and quality. Surprisingly, it has now been found that compounds of formula I may be readily and efficiently prepared from their halo precursors at atmospheric pressure using a transition metal catalyst and ammonium formate as a hydrogen source in the presence of a polar solvent, optionally at an elevated temperature. Advantageously, the product formula I compounds are obtained in good yield and high quality. The reaction is shown in flow diagram I.

Flow Diagram I

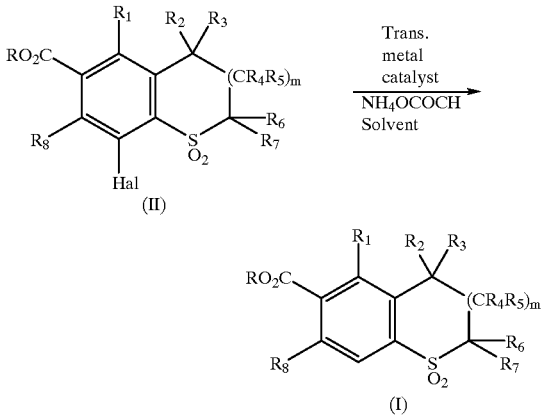

Polar solvents suitable for use in the process of the invention include alkanols, carboxylic acids or mixtures thereof, preferably methanol, ethanol or a mixture thereof.

Transition metal catalysts suitable for use in the inventive process include those transition metals commonly used in catalytic hydrogenation procedures such as Pt, Pd, Ni, Rh and similar conventional transition metals, preferably Pd. A catalytic amount designates that amount of catalyst required to facilitate the reaction and may range from an equimolar amount to a trace amount, preferably about 5 mole % to 20 mole %.

Suitable reaction temperatures useful in the inventive process may range from ambient temperatures to the reflux temperature of the solvent or solvent mixture. In general, increased reaction temperature leads to increased reaction rate and drives the reaction to completion. However, excessively high temperatures may be detrimental and are not required. Preferable reaction temperatures are about 25° C.–200° C., more preferably about 50° C.–150° C.

Stoichiometrically, the inventive process requires at least 2 molar equivalents of ammonium formate in order to go to completion, however excess amounts of ammonium formate may be employed without detrimental effect.

Therefore, in accordance with the process of the invention, a compound of formula II, preferably wherein Hal is chlorine, is admixed with a polar solvent, preferably an alkanol, acetic acid or a mixture thereof, treated with at least 2 molar equivalents of ammonium formate, preferably 3 to 5 molar equivalents, and a catalytic amount of a transition metal catalyst, preferably Pd on carbon (Pd/C) at temperatures ranging from ambient temperatures to the reflux temperature of the solvent, preferably about 25° C.–200° C., the inventive process are those compounds wherein Hal is Cl; m is 0; and $R_2$ and $R_3$ are each independently $C_1$–$C_4$alkyl.

Thiochroman and dihydrobenzothiophene herbicidal agents may be prepared from compounds of formula II via the inventive process to form the intermediate compound of formula I; when R is $C_1$–$C_4$alkyl, hydrolyzing the formula I compound to the corresponding carboxylic acid of formula III; and reacting the formula III acid with an hydroxypyrazolyl compound of formula IV to obtain the arylcarbonyl compound of formula V, optionally reacting the formula V compound with a sulfonyl chloride of formula VI to obtain the arylcarbonyl compound of formula VII. The formula V and formula VII arylcarbonylthiochromans and dihydrobenzothiophenes are potent herbicidal agents. The reaction sequence is shown in flow diagram II wherein $R_{10}$ is $C_1$–$C_4$alkyl; $R_{11}$ is H or $C_1$–$C_4$alkyl; and $R_{12}$ is $C_1$–$C_6$alkyl or phenyl optionally substituted with one to three halogen, $NO_2$, $C_1$–$C_4$alkyl, or $C_1$–$C_4$alkoxy groups.

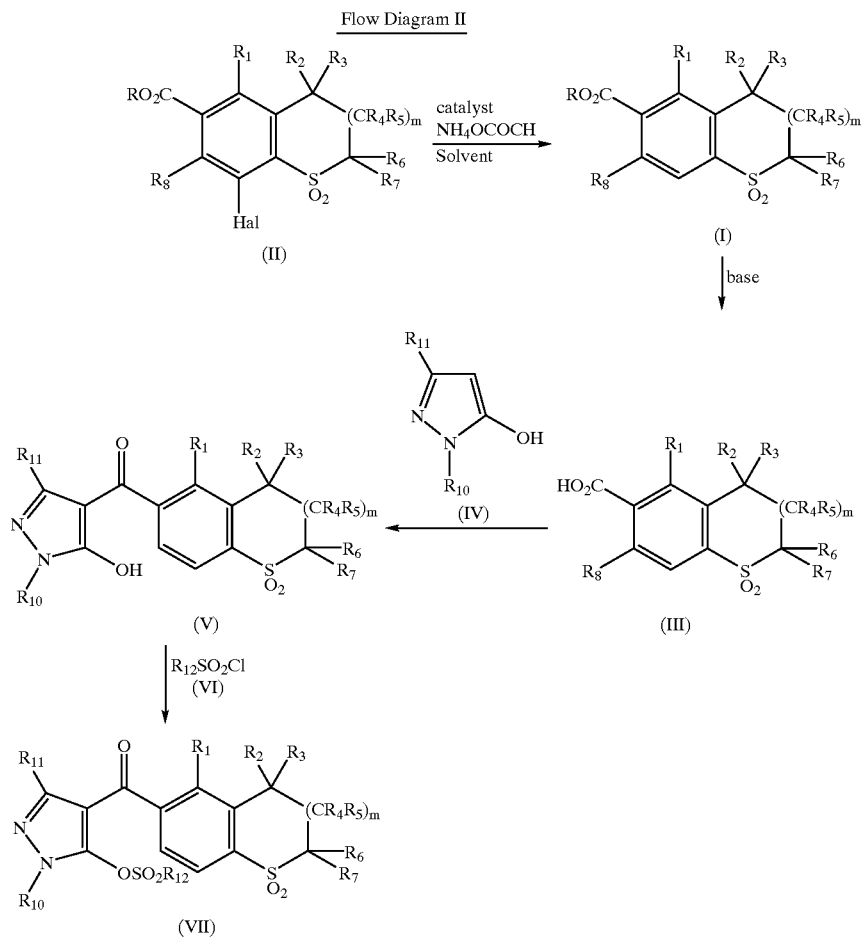

Flow Diagram II more preferably about 50° C–150° C., to obtain the desired formula I compound.

Compounds of formula II preferred for use in the inventive process include those compounds of formula II wherein Hal is Cl; m is 1; and $R_2$ and $R_3$ are taken together with the atom to which they are attached to represent C=$NOR_9$. Another group of formula II compounds preferred for use in The herbicidal agents of formula V and formula VII and their preparation from compounds of formula I are described in U.S. Pat. Nos. 5,506,194 and 5,607,898. The hydrolysis and sulfonation steps described above may be accomplished using conventional methods. The coupling of the hydroxypyrazole compound of formula IV and the subsequent rearrangement to the desired compound of formula V may be performed using standard methods such as those described in U.S. Pat. No. 5,506,194 and U.S. Pat. No. 5,607,898, i.e. in the presence of a base and a dehydrating agent.

For a more clear understanding of the invention, the following examples are set forth below. These examples are merely illustrative and are not understood to limit the scope of underlying principles of the invention in any way. Indeed, various modifications of the invention, in addition to those shown and described herein, will become apparent to those skilled in the art from the following examples and the foregoing description. Such modifications are also intended to fall within the scope of the appended claims.

The terms $^1$HNMR and $^{13}$CNMR designate proton and carbon 13 nuclear magnetic resonance, respectively. The term IR designates infrared spectroscopy. HPLC designates high performance liquid chromatography.

EXAMPLE 1

Preparation of Ethyl 2,3-Dihydro-5-methyl-4-oxo-4H-1-benothiopyran-6-carboxlyate, 1,1-dioxide, 4-(0-methoxyloxime)

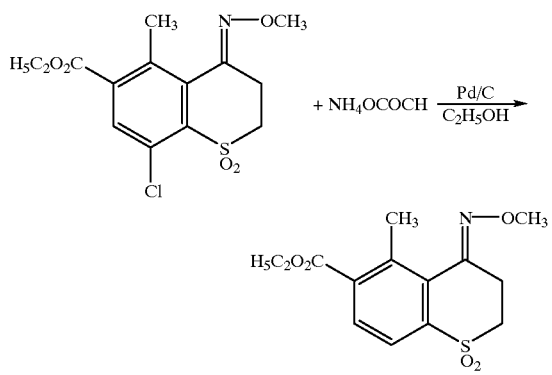

A stirred mixture of ethyl 8-chloro-2,3-dihydro-5-methyl-4-oxo-4H-1-benzothiopyran-6-carboxylate, 1,1-dioxide, 4-(0-methyloxime) (800 g, 2.31 mol) in ethanol is treated with ammonium formate (729.4 g, 11.57 mol) and with 10% Pd/C (50% water) (800 g, 0.375 mol), heated to reflux temperature over a 1 hour period, held at reflux temperature for about 4 hours (until reaction is complete by HPLC analysis), stirred at ambient temperatures for 19 hours and filtered through a bed of diatomaceous earth. The filtercake is slurried in tetrahydrofuran (THF) and filtered several times. All filtrates are combined, concentrated to about ⅓ the original volume and filtered though a bed of diatomaceous earth. The filtercake is washed with additional THF. The filtrates are combined, labelled filtrate A and set aside.

The above procedure is repeated using the same quantities of reactants. The filtrates from this repeated reaction are combined and labelled filtrate B. Filtrates A and B are combined and concentrated in vacuo to about ⅕ the original volume, poured into water (about 6-fold volume) and filtered. The filtercake is washed with water and dried in vacuo at 55°–60° C. for 16 hours to give the title product as a pale yellow solid, 1,230.0 g (85.4% yield), 98.1% pure by HPLC analysis, identified by $^1$HNMR, $^{13}$CNMR and IR analyses.

EXAMPLE 2

Preparation of Ethyl 2,3-Dihydro-3,3,4-trimethylbenzo[b]thiophene-5-carboxylate, 1,1-dioxide

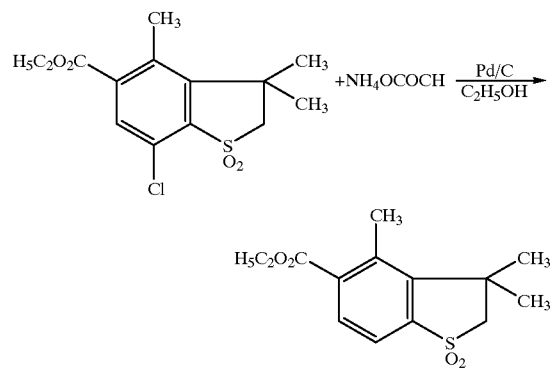

Using essentially the same procedure described in Example 1 and substituting ethyl 7-chloro-2,3-dihydro-3,3,4-trimethylbenzo[b]thiophene-5-carboxylate, 1,1 -dioxide as starting material, the title product may be obtained and identified by $^1$HNMR, IR and mass spectral analyses.

EXAMPLE 3

Preparation of 2,3-Dihydro-3,3,4-trimethylbenzo[b]thiophene-5-carboxylic acid, 1,1-dioxide

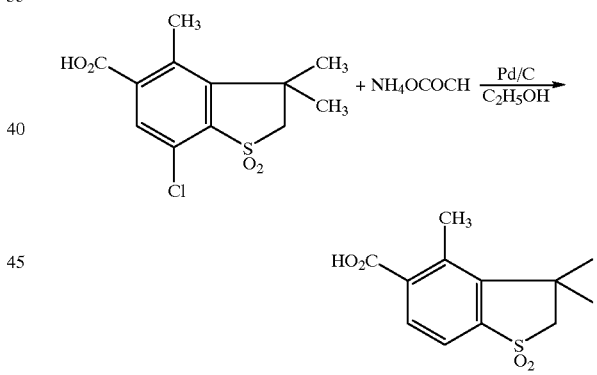

A mixture of 7-chloro-2,3-dihydro-3,3,4-trimethylbenzo[b]thiophene-5-carboxylic acid, 1,1-dioxide (1.0 g, 3.46 mmol), ammonium formate (1.0 g, 15.9 mmol) in ethanol, under nitrogen, is treated with 10% Pd/C (50% water) (0.50 g, 0.235 mmol Pd), heated at reflux temperature for 1 hour (reaction complete by HPLC analysis), cooled to room temperature and filtered through diatomaceous earth. The filtercake is washed with ethanol. The filtrates are combined and concentrated in vacuo to give a residue. The residue is taken up in aqueous NaOH, cooled to 5° C. and acidified to pH 1 with concentrated HCl to give a precipitate. The mixture is filtered. The filtercake is washed with water and air dried to give the title product as a white solid, 0.80 g (91% yield) 99.3% pure by HPLC analysis, identified by $^1$HNMR.

EXAMPLE 4

Preparation of Ethyl 4,4,5-trimethylthiochroman-6-arboxylate-1-dioxide

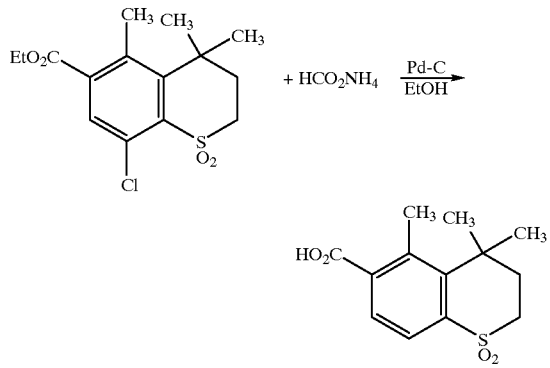

EXAMPLE 5

Preparation of Ethyl 4,4,5-trimethylthiochroman-6-carboxylate-1,1-dioxide

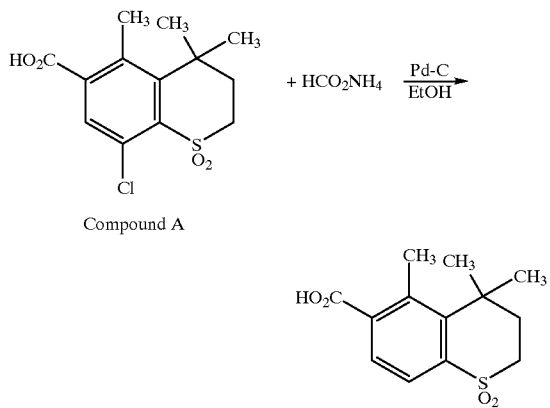

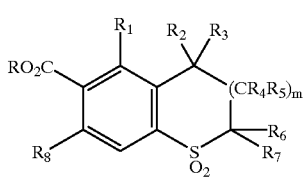

Compound A

What is claimed is:

1. A process for the preparation of a compound of formula I

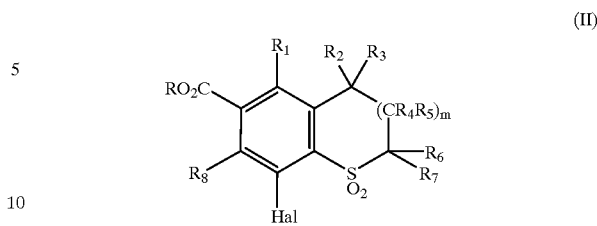

wherein

R and $R_1$ are each independently H or $C_1$–$C_4$alkyl;

$R_2$ and $R_3$ are each independently H, $C_1$–$C_4$alkyl or $R_2$ and $R_3$ may be taken together with the atom to which they are attached to form a group C=NOR$_9$ or C=O;

$R_4$, $R_5$, $R_6$, $R_7$, $R_8$ and $R_9$ are each independently H or $C_1$–$C_4$alkyl; and m is 0 or 1 which process comprises reacting a compound of formula II

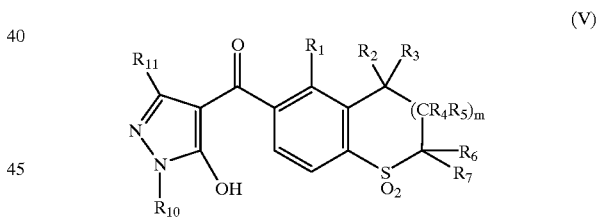

wherein Hal is Cl, Br or I and R, $R_1$, $R_2$, $R_3$, $R_4$, $R_5$, $R_6$, $R_7$, $R_8$ and m are as described hereinabove with a catalytic amount of a transition metal catalyst and at least two molar equivalents of ammonium formate in the presence of a polar solvent optionally at an elevated temperature.

2. The process according the claim 1 wherein the solvent is a $C_1$–$C_6$alkanol, a $C_1$–$C_6$carboxylic acid, or a mixture therof.

3. The process according to claim 1 wherein the transition metal is Pd.

4. The process according to claim 1 wherein Hal is Cl.

5. The process according to claim 1 wherein the temperature is about 25° C.–200° C.

6. The process according to claim 1 wherein m is O and $R_2$ and $R_3$ are each independently $C_1$–$C_4$alkyl.

7. The process according to claim 1 wherein m is 1; $R_2$ and $R_3$ are taken together with the atom to which they are attached to form a group C=NOR$_9$; and $R_9$ is $C_1$–$C_4$alkyl.

8. The process according to claim 4 wherein $R_1$, $R_2$ and $R_3$ are methyl; $R_6$, $R_7$ and $R_8$ are H; and m is O.

9. The process according to claim 4 wherein $R_1$ is methyl; $R_2$ and $R_3$ are taken together with the atom to which they are attached to form a group C=NOR$_9$; $R_9$ is methyl; $R_4$, $R_5$, $R_6$, $R_7$ and $R_8$ are H; and m is 1.

10. The process according to claim 5 wherein the temperature is about 50° C.–150° C.

11. A process for the preparation of a herbicidal compound of formula V or formula VII

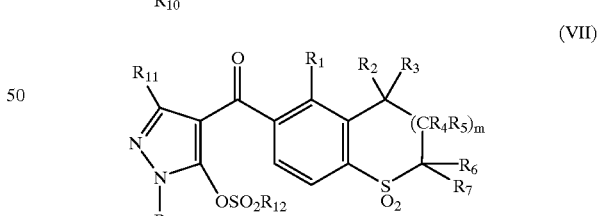

wherein $R_1$, $R_2$, $R_4$, $R_5$, $R_6$, $R_7$, $R_8$, $R_9$ and $R_{11}$ are each independently H or $C_1$–$C_4$alkyl;

$R_2$ and $R_3$ are each independently H or $C_1$–$C_4$alkyl or $R_2$ and $R_3$ may be taken together with the atom to which they are attached to form a group C=NOR$_9$ or C=O;

$R_{10}$ is $C_1$–$C_4$alkyl;

$R_{12}$ is $C_1$–$C_6$alkyl or phenyl optionally substituted with one to three halogen, $NO_2$, $C_1$–$C_4$alkyl or $C_1$–$C_4$alkoxy groups; and m is 0 or 1 which process comprises the following steps:
(a) reacting a compound of formula II

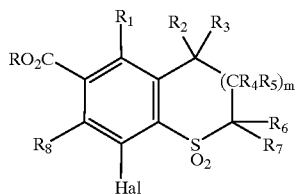
(II)

wherein Hal is Cl, Br, or I with a catalytic amount of a transition metal catalyst and at least two molar equivalents of ammonium formate in the presence of a polar solvent optionally at an elevated temperature to give a compound of formula I

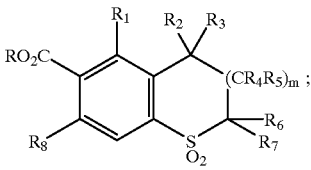
(I)

(b) hydrolyzing said formula I compound wherein R is $C_1-C_4$alkyl with base to give the corresponding carboxylic acid; and
(c) reacting said carboxylic acid with a compound of formula IV

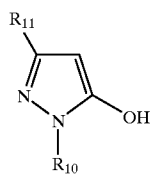
(IV)

to obtain the desired herbicidal compound of formula V, optionally reacting said formula V compound with a sulfonyl chloride $R_{12}SO_2Cl$ to obtain the desired herbicidal compound of formula VII.

12. The process according to claim 11 wherein the transition metal catalyst in step a is Pd.

13. The process according to claim 12 wherein the polar solvent in step a is a $C_1-C_6$alkanol; a $C_1-C_6$carboxylic acid; or a mixture thereof.

14. The process according to claim 13 for the preparation of a formula V or formula VII herbicidal compound wherein m is 1; $R_2$ and $R_3$ are taken together with the atom to which they are attached to form a group C=$NOR_9$; and R9 is $C_1-C_4$alkyl.

15. The process according to claim 13 for the preparation of a formula V or formula VII herbicidal compound wherein m is 0; and $R_2$ and $R_3$ are each independently $C_1-C_4$alkyl.

* * * * *